United States Patent
Karlsson et al.

(10) Patent No.: US 8,133,395 B2
(45) Date of Patent: Mar. 13, 2012

(54) AUTOMATED COLUMN PACKING METHOD

(75) Inventors: Johan F. Karlsson, Uppsala (SE); Joakim Lundkvist, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 12/994,166

(22) PCT Filed: May 26, 2009

(86) PCT No.: PCT/SE2009/050600
§ 371 (c)(1),
(2), (4) Date: Nov. 23, 2010

(87) PCT Pub. No.: WO2009/145714
PCT Pub. Date: Dec. 3, 2009

(65) Prior Publication Data
US 2011/0077766 A1    Mar. 31, 2011

(30) Foreign Application Priority Data
May 30, 2008 (SE) .................................. 0801282

(51) Int. Cl.
*B01D 15/08* (2006.01)
(52) U.S. Cl. ..................... 210/656; 210/143; 210/198.2
(58) Field of Classification Search ................... 210/635, 210/656, 143, 198.2, 232; 141/12, 73, 80
See application file for complete search history.

(56) References Cited

U.S. PATENT DOCUMENTS

| 7,452,471 B2 * | 11/2008 | Windahl ........................ 210/656 |
| 2006/0219616 A1 | 10/2006 | Noyes et al. |
| 2007/0012626 A1 | 1/2007 | Andersson et al. |
| 2007/0090053 A1 * | 4/2007 | Windahl ........................ 210/656 |
| 2007/0262021 A1 | 11/2007 | Perreault et al. |
| 2011/0077766 A1 * | 3/2011 | Karlsson et al. ............... 700/110 |

* cited by examiner

*Primary Examiner* — Ernest G Therkorn

(57) ABSTRACT

A method for automatically without any required manual interaction packing a media bed in a column (3) from a slurry being a dispersion of said media particles and a liquid, said method comprising the steps a)-f) which all are performed automatically: a) filling the column (3) with a certain volume of slurry; b) packing a media bed from the slurry to a predefined target bed height or a predefined target bed compression; c) testing the separation efficiency of the packed bed; d) automatically unpacking the bed if test results not are acceptable or alternatively flow conditioning the packed bed if test results not are acceptable and return to c); e) calculating new volume of slurry to be filled into the column based on the test results; f) repeat from a).

6 Claims, 2 Drawing Sheets

AUTOMATED COLUMN PACKING METHOD

CROSS-REFERENCE TO RELATED APPLICATIONS

This application is a filing under 35 U.S.C. §371 and claims priority to international patent application number PCT/SE2009/050600 filed May 26, 2009, published on Dec. 3, 2009 as WO 2009/145714, which claims priority to application number 0801282-5 filed in Sweden on May 30, 2008.

FIELD OF THE INVENTION

The present invention relates to a media packing system for columns and media packing methods for use in columns. More specifically, the invention relates to methods for improving the quality, ease and consistency of packing chromatography media into chromatography columns.

BACKGROUND OF THE INVENTION

Columns used in liquid chromatography typically comprise a tubular body enclosing a packed bed of porous chromatography medium through which a carrier liquid flows, with separation taking place by material collection between the carrier liquid and solid phase of the porous medium. Typically, the medium is enclosed in the column as a packed bed formed by consolidating a suspension of discrete particles, known as slurry that is pumped, poured, or sucked into the column. Consolidation of the slurry into a consolidated packed bed is achieved by compressing the slurry so that it is packed into a volume, which is less than the volume that it would have occupied if it had been allowed to settle under the influence of gravity to form a sedimented bed. The efficiency of subsequent chromatographic separation relies strongly on 1) the liquid distribution and collection system at the fluid inlet and outlet of the packed bed, 2) on the spatial orientation (also know as the packing geometry) of the media particles in the packed bed, and 3) on the compression of the packed bed. If the compression of the packed bed is too low then chromatographic separations performed on that bed suffer from "tailing" and, generally, such insufficiently compressed beds are unstable. If the compression of the packed bed is too high then chromatographic separations performed by the bed suffer from "leading" and such over-compressed beds can affect throughput and binding capacity, and, in general, give much higher operating pressures. If the compression is optimum, then the separation peaks formed during use exhibit much less leading or tailing and are substantially symmetrical. The optimum degree of compression required for a column is determined experimentally for each column size (width or diameter), bed height, and media type.

Prior to any separation process the column and the bed have to be prepared. Before the column is filled with slurry the column, hoses to/from the column and valves connected to the column often needs to be primed. This means to purge away air from the column and from the hoses connected to the system. Usually liquid is flowed through the system and column to purge the air away. After the column has been filled, either by means of the liquid flow through the bed support or through spray nozzles, it can be pressurized to force the last remaining air out of the column. This can be achieved by continuing to pump liquid into the column against a closed outlet and then opening the outlet to release pressure or by running the moveable adapter downwards fast, thereby expelling air through the bed supports, possibly one at a time. After the priming the column often also needs to be sanitized. Then the column can be filled with slurry and the packing procedure takes place. The process of bed formation is called 'the packing procedure' and a correctly packed bed is a critical factor influencing the performance of a packed bed. One of the primary goals of the packing procedure is to provide a bed, which is compressed by the optimum amount of compression, i.e. the optimum compression factor. The height of the bed which often is user defined when it is optimally compressed is called the target compressed bed height.

Large-scale columns, can be prepared by suctioning or injecting into the column a predetermined volume of slurry having a specified or known concentration of media particles. Once the predetermined volume of slurry has been delivered into the column it needs to be consolidated and compressed by for example moving a movable adapter down the longitudinal axis of the column towards the bottom of the column, normally at a constant speed push both liquid and particles towards the bottom of the column. The excess liquid during this procedure is expelled at the column outlet, while the media particles are retained by means of a filter material, a so-called 'bed support', with pores too small to allow the media particles to pass through. The packing process is complete once the packed bed has been compressed by the optimum degree of compression. The packing process is considered successful if the compressed bed allows for a good and robust chromatographic performance. There are alternative ways of packing that can be used in this invention. For example a flow can be applied to force the particles in the slurry to move towards the outlet of the column, instead of moving an adapter downwards. A further alternative is to use spray nozzles spraying in slurry until a packed bed is achieved. These methods will be further described below. However, packing such an optimally compressed bed of chromatography media in a chromatography column by manual means is not easy to accomplish in practice due to the fact that the quality of the final packed bed depends to a great extent on the skill of the operator. During filling and subsequent packing of the column, the operator manually selects and adjusts all packing parameters such as valve positions, pump speed, adapter's speed of movement, etc. The operator has to measure the slurry concentration in order to decide how much slurry that should be filled into the column. If the measure of the slurry concentration is not exact (which is often the case because it is hard to measure the slurry concentration exactly) the volume of the slurry filled into the column is not optimal and the consolidated bed will settle at a bed height that was not expected (as calculated from the measured slurry concentration) and hereby the target compression can not be achieved at target bed height. Furthermore, the operator also has to judge the point when the adapter starts compressing the bed. This point is used to calculate how much further the adapter must move in order to obtain the required amount of compression. Mistakes in the selection of any of the packing parameters normally lead to a poorly performing column. Further, in columns equipped with a transparent tube it may be difficult, and in columns equipped with a non-transparent tube such as stainless steel it is impossible, to judge by eye when compression of the bed actually starts and a significant error at this point makes it impossible to obtain an optimally compressed bed.

There is also a risk of damaging the media and the column if the user takes wrong decisions.

When the media bed has been packed in the column an efficiency test is sometimes performed in order to judge if the packed bed is good enough for use. This could be for example a pulse test, a transitional test or a test of pressure/flow properties. If the results from the tests show that the packed bed is of unacceptable quality the bed needs to be unpacked and then repacked in order to provide a packed bed that is acceptable.

All these steps that need to be performed are of course time consuming. Operator errors are common which leads to time consuming and costly repacking.

Therefore, there is a need for a system and method for the accurate and reproducible packing of chromatography media into chromatography columns.

SUMMARY OF THE INVENTION

An object of the invention is to provide a column packing system and a method for packing media into columns in order to overcome the drawbacks of the prior art systems.

This is achieved in a method, in a computer program product and in a control unit.

Hereby all these steps are performed automatically without the need of any manual interaction. Since both filling, packing, testing, possibly unpacking and repacking is included in this automatic process a packed bed that is acceptable according to the tests performed will finally be provided without any interaction from the user.

Suitable embodiments are described in the dependent claims.

DETAILED DESCRIPTION OF THE INVENTION

The presently preferred embodiments of the invention are described with reference to the drawings. The descriptions of the preferred embodiments are exemplary and are not intended to limit the scope of the invention.

As used herein and in the appended claims:

The term "column" is intended to include the terms "vessel" and "cell", as well as any other structure utilized by practitioners of the separation arts, to effect a separation, and/or reaction, and/or catalyzation, and/or extraction of components from an admixture by bringing the admixture into contact with solid or liquid exchange media, known as the packed bed.

The term "slurry" is a dispersion of media particles and liquid.

The term "longitudinal direction of flow" refers to the direction of flow from an inlet towards an outlet within a column. "Longitudinal" is used consistently to designate the dominant flow path of fluid through a cell without regard to direction.

The term "distribution system" refers to structures through which fluids are introduced to a column and dispersed over the whole cross-sectional area of the column and the term "collection system" refers to structures used to collect fluids from a column.

The term "sedimented bed height" refers to the height of a bed of media particles which is obtained when a bed is formed after the media particles in a slurry are allowed to sediment under the influence of gravity only—such a bed is called a "sedimented bed".

The term "consolidated bed height" refers to the height of a bed of media particles that is obtained when a bed is formed in a column while the media particles in a slurry are forced to sediment when a flow of fluid is applied through the column in the longitudinal direction of flow either by 1) pumping liquid into the column, 2) by pumping liquid out of the column, or 3) by the movement (for example, the descent) of a movable adapter, which forces liquid out of the column— such a bed is called a "consolidated bed".

The term "compressed bed height" refers to the height of a bed of media particles in a column that is obtained when a consolidated or sedimented bed has been compressed, for example by contact with, and further movement of, a movable adapter or the like, or by pumping fluid through the column at a higher rate than that used during consolidation of the bed— such a bed is called a "compressed bed".

The term "compression factor" is defined as (the sedimented bed height)/(the compressed bed height) and the term "packing factor" is defined as (the consolidated bed height)/(the compressed bed height). Hereafter, when packing factor is used it should be understood that the compression factor could be used instead.

Figure 1:
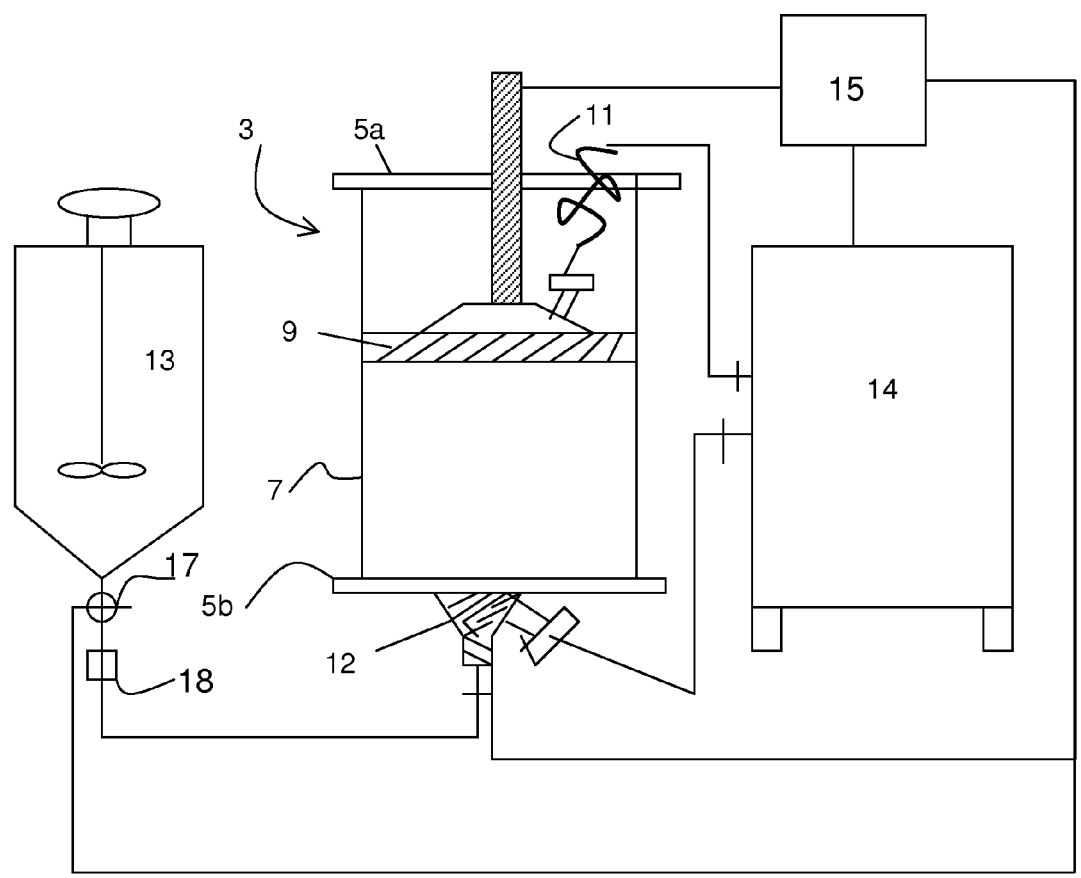
FIG. 1 is a schematic diagram of a media packing system according to one embodiment of the invention.

FIG. 1 is a schematic view of a column packing system according to one embodiment of the invention. The system comprises a column 3 which comprises upper lid or flange 5a and lower end plate 5b surrounded by a cylindrical column wall 7. Positioned between the lid or flange 5a and lower end plate 5b in the column 3 is a movable adapter 9 (which may be provided with a liquid distribution system, not shown, intended to distribute incoming liquid substantially evenly over the cross-section of the column 3, and a bed support, not shown, extending over the cross-section of the column with a mesh fine enough to prevent bed particles from passing through it) connected to a column inlet 11 connectable to a liquid delivering system 14 which delivers liquids such as sample mixtures, eluents, buffers etc. Movable adapter 9 is movable in the longitudinal direction of the column by an actuator (not shown), such as an electric, hydraulic or pneumatic motor or piston/cylinder actuator.

Slurry can be sucked into the column 3 through a nozzle or valve 12 positioned in the bottom of the column. The nozzle or valve 12 is connected to a slurry tank 13 possibly via a slurry tank valve 17. Movable adapter 9 is provided with a positioning means (not shown) to determine the position ("x") of the movable adapter relative to a fixed level, for example the upper side of the lower end plate 5b, and a signal corresponding to the distance x is sent to a control unit 15 which in this example is connected to the liquid delivering system 14 and can thereby control the opening and closing of valves to and from the column. The control unit 15 could however instead be built into the liquid delivering system 14. The control unit 15 is further connected to the adapter actuator, to the slurry tank valve 17 and to the nozzle or media valve 12 to control these by suitable means. The control unit 15 can also in one embodiment of the invention be connected to an inline slurry concentration measurement device 18 preferably positioned somewhere near the outlet from the slurry tank. The operation of the actuator and the corresponding up or downwards movement of the movable adapter 9 is controllable by the control unit 15. Control unit 15 preferably comprises hardware and software for controlling the operation of the column 3. The control unit 15 controls for example the opening and closing of valves (i.e. valves between liquid delivering system and inlet and outlet of the column, the media valve 12 and the slurry tank valve 17) and the speed of the movable adapter movement.

In FIG. 1 one example of a column is shown. However there are other types of columns whose packing processes also can be automated according to the invention. For example the packing does not necessarily need to be performed by moving an adapter downwards. Another example of a packing process that can be automated according to the invention is a column where the adapter is placed at the intended final packed bed height and the column is filled and packed at the same time through the nozzle in the top of the column. As slurry is being sprayed into the column, excess liquid will leave the column through the bottom bed support. The particles of the slurry will be retained by the bed support and a bed will build up from the bottom. When the correct amount of slurry has been delivered from the slurry tank to the column, the packing pump can be shut off and the nozzle retracted. This packing can be automated by either measuring the amount of slurry in the tank by weight or by a flow meter at the inlet of the column. For a column with a spray nozzle the spray action can be used to break up the bed and unpack the column. Eventually the bed is broken up and the slurry can be pumped out through the column.

Another possible solution is to combine this packing method with a moveable adapter. The column can be packed as described above but this time the bed is not compressed. Instead the adapter is used for the final compression.

The column described in FIG. 1 is also possible to pack in another way than described above. Instead of creating the liquid flow through the downwards movement of the adapter, it can remain in the filling position while a liquid flow through the top bed support is used to consolidate or pack the bed. The flow rate can be varied so that the bed is first consolidated and then packed. At the end, when the bed is compressed through flow the adapter can be lowered to the bed surface to prevent it from expanding.

Figure 2:
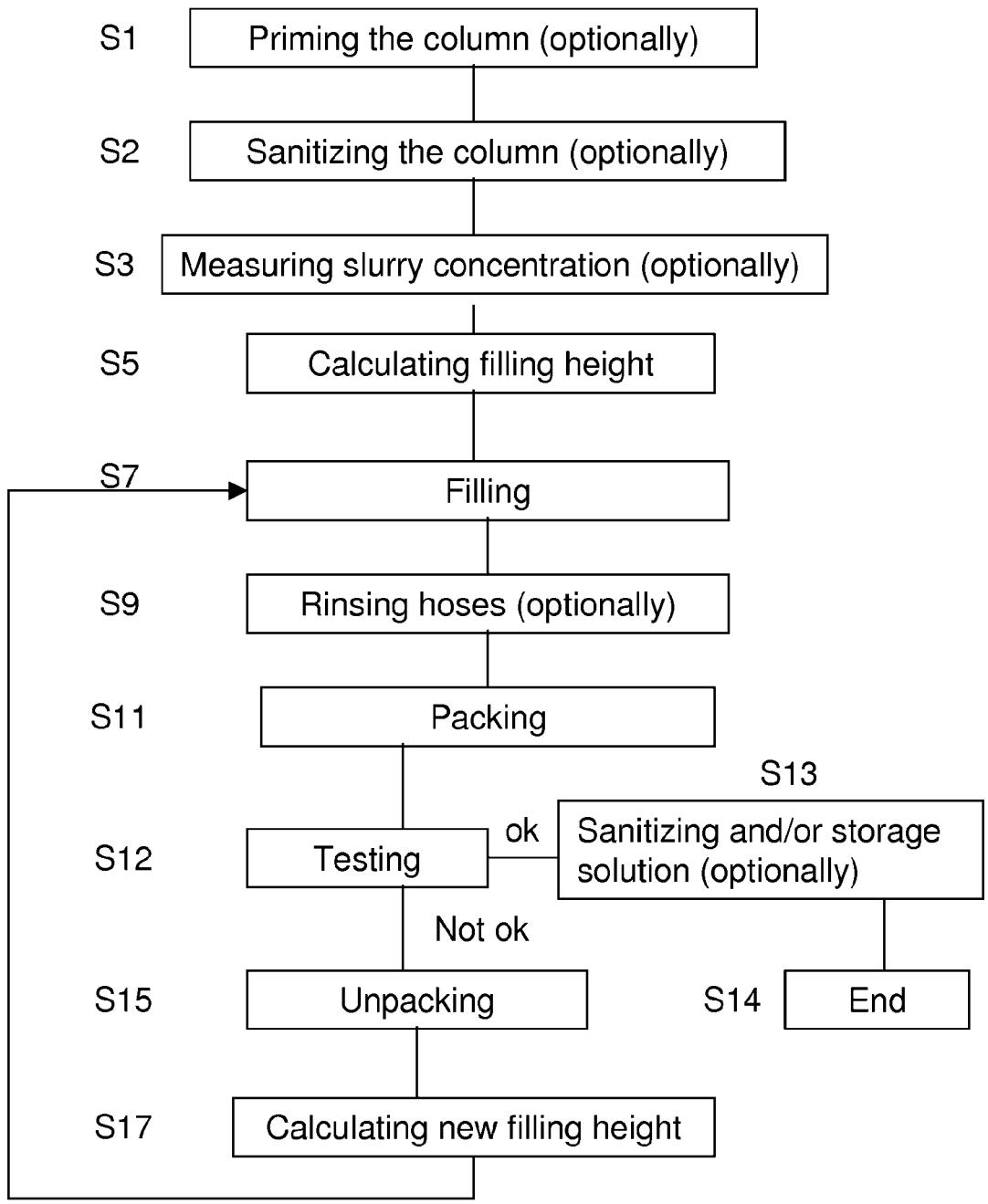
FIG. 2 is a flow chart describing the packing method according to one embodiment of the invention.

According to this invention a fully automated process for packing a column is provided. FIG. 2 is a flow chart of the packing process according to one embodiment of the invention.

The process can comprise the following steps:

S1: Priming the system (this step is optionally included into the automated process according to the invention), i.e. to purge away air in the system comprising both hoses, valves and column. This can be done according to well known methods. One example how this can be done is to prime all liquid connections to the column and tanks with liquid first by pumping liquid through all relevant hoses. Then the column is filled with liquid until as much air has been pushed out of the column as possible and then the adapter is run down expelling excess air and liquid through first the top screen and then through the bottom screen or vice versa.

S2: Sanitization of the column is optionally included into the automated process.

S3: In one embodiment of the invention the slurry concentration is measured automatically inline.

S5: Optionally the filling height (how much slurry that should be filled into the column) can be calculated automatically. The filling height is calculated based on target bed height, packing factor and slurry concentration. Alternatively the column can be filled to a predetermined height or by a predetermined volume of slurry.

S7: Filling the column with slurry: The filling speed can be chosen to suit the specific medium of use or environmental conditions such as slurry concentration, viscosity and temperature. A passage between the slurry vessel and the column, such as a valve which can be controlled automatically, must be open so that when the adapter moves up from the bottom position with a predetermined speed, the slurry is pulled by under-pressure from the tank into the column. The column can also be filled by the means of a pump, either pushing up the adapter as the slurry is being pumped into the column or by filling the column with slurry with the adapter already in the correct filling position. Instead of a pump, a pressurized tank filled with slurry can be used. At the calculated filling height or filling volume in the case of a pump, the adapter will stop (if it is moving) and the valve will close.

S9: An automatic rinse of the hoses can then optionally be included. This is in order to avoid any medium remaining in the hoses after filling. Remaining medium may plug the hoses and thereby making later procedures more difficult.

S11: Packing of the medium bed. In the example with a movable adapter one of the mobile phases flow path (in most cases the bottom) will open and the adapter will start moving down at a pre-defined speed, which depends on the method of packing and the properties of the medium being packed. I.e. in dependence of which choices or inputs that was initially made by the user the control unit chooses which speed to use for the adapter during packing. The liquid inside the column will start moving downwards at the same speed as the adapter and out through the permeable bottom screen and the bottom mobile phase valve. The particles of the chromatography medium will not pass the screen, but will be stopped by a filtering action and start to form a consolidated bed. At some point all particles will have formed a bed and the adapter will come into contact with the packed bed. The adapter will continue with a constant speed as before (the speed can also be changed). The point when the adapter meets with the bed can be detected by means of pressure, optical sensors, change in actuator output or any other measurable force. At this point the bed is loosely packed and in many cases need further compression for it to obtain the desired separation performance, the desired long-term bed stability and resistance to the compressive forces due to flow through the packed bed. If the adapter continues to move down into the bed, the latter will start compressing much like a spring. The amount of compression needed after the point of bed and adapter contact depends on the adapter speed, the packing buffer, temperature, column diameter, the bed height but foremost on the properties of the chromatography medium. The amount of compression needed is defined as the packing factor, which is the ratio of the uncompressed bed height to the compressed bed height. The packing factor for a specific medium and the current adapter speed determines how much further the bed should be compressed and thus how much further the adapter will move before reaching the final bed height. Provided the entered slurry concentration is correct, the adapter will stop at the intended target bed height. This feature also allows for a method without any detection of the bed as the final bed height can be calculated on input data. The adapter will then simply move to the predetermined position based only on calculations. If variations in final bed height or packing factor can be allowed, the software can be programmed to take such considerations into account. This allows for some input errors or slurry concentration measurement errors. At the end of this procedure, the column is packed. As described above there are also other methods of packing possible to use in this invention.

S12: Efficiency testing. In many cases there is a desire to measure the homogeneity or efficiency of the packed bed. This can be made in many ways, the most common being pulse tests or by transitional analysis. The pump system can be equipped with the necessary valves and detectors to perform these tests according to a pre-programmed method taking into account the type of media, the bed height and the column volume.

Various tests that can be used to assess the quality of the bed are listed and outlined below. One or more tests can typically be used and the most common ones are included here. That is, the tests shouldn't be limited to the ones here.

Pulse test: A pulse test is a test to determine the separation efficiency in a packed bed and is normally reported as HETP (Height Equivalent to a Theoretical Plate) and Asymmetry that describes the skewness of the peak. A small pulse, the volume often equal to 1% of the column volume, of a substance that can be detected by for example UV or conductivity is injected into the column. It is then eluted by a substance that moves it along the column until it exits the column. The width of the resulting peak determines the separation efficiency of the column. The wider, the more mixing has occurred in the column and the lower the efficiency is.

Transitional test: A transitional test is similar to a pulse test. The difference is that instead of injecting a pulse, the new solution with different conductivity is continuously pumped into the column. At the outlet the transition from solution A to solution B is seen as a step like shape. The first derivate of the step is basically the same as the pulse and can be evaluated according to the same principles.

Pressure/flow: A pressure/flow test can be run to determine if the optimal compression is reached. The pressure drop at a certain flow velocity is very sensitive to the bed compression and a deviation from standard values may indicate that the beds is not optimally compressed.

Stability: A stability test is basically the comparison of two pulse test, the first immediately after packing and the other after extensive flowing of the bed, for example overnight. If the results differ too much between the two tests it indicates that performance of the bed will change over time of use. This is generally not desirable.

Void measurement: The void fraction of the packed bed, i.e. the volume between particles, is to a great extent determined by compression. A void fraction measurement can reveal if the optimal compression was achieved or not. The test is carried out as the pulse test, but utilizes a tracer molecule that is too large to enter any pores of the particles and therefore only travels in the void volume of the bed.

If the test results are in accordance with predetermined specifications, the column is ready for use in a chromatographic separation—step S14 (possible after another sanitization step S13). In the case of a result outside predetermined specifications the system can start the unpacking procedure automatically—step S15. This analysis of the test results is performed automatically and the decision is based on pre-defined acceptance criteria.

S13: The test results were in accordance with predetermined specifications and another sanitization step is possibly performed. The column can also possibly be transferred into a storage solution. Hereby the column can keep its properties and sanitization during storage.

S14: An acceptable packed bed is achieved and the process according to the invention is finished.

S15: Unpacking. If the test results fall outside predetermined specifications, i.e. if the packed bed did not fulfil acceptance criteria, the column can according to the invention be automatically unpacked (in order to be packed again under somewhat changed conditions). The column can be unpacked in many ways, by the combined effects of the pump system delivering liquid flow in through either of the mobile phases, the upwards or downwards movement of the adapter and by utilizing valves through which slurry or buffer can be pumped or sprayed in and out of the column. The whole process can be monitored and controlled by measuring critical parameters such as column pressure, adapter position and speed and flow rate and direction. If the column is equipped with means for spraying liquid or slurry into the column, these pumps can be automated as well. In this case the bed structure is broken by the spray action and the resulting slurry can be pumped or pushed by the adapter out of the column. Alternatively the bed can be expanded by running the adapter upwards at the same time as liquid is delivered through the bottom mobile phase. This will lift the bed from the bottom screens and allow it to expand to and/or past the point of the uncompressed bed. Pushing the bed up with a liquid layer underneath will make the bed to break apart and fall to the bottom. A push of liquid from the top column inlet can help to speed up the break-up of the bed. At this point, the bottom valve is opened and a slow liquid flow through the bottom screen is started to keep media from being packed against the bottom screen again. The adapter is run downwards and thereby forcing the slurry to exit through the bottom media valve. Both the adapter speed and the liquid speed through the bottom screen can vary throughout the process to yield the best unpacking conditions and to reach a certain end slurry concentration. The adapter is run all the way down to its bottom position and the remaining media can be flushed out. The column is now ready for another cycle. Any combinations of the following parameters can be used to unpack the column in one or more steps; expansion height, pump flow rates in the different steps, adapter speed, flushing speed and so on can be controlled to yield the unpacking procedure of choice. Another option to unpack the column is to pull and push slurry back and forth from and to the column to break up the bed. Yet another option is to close all column inlets and create an under-pressure in the column which pulls the bed apart. Since the system can calculate medium volume and added liquid volume the unpacking can be made towards a specific target concentration, which could be as high as possible if the medium is intended for storage or disposal or any suitable concentration for the next packing attempt.

An alternative to unpacking and repacking can be to conditioning the packed bed by flowing any liquid such as water or packing buffer through the bed at a high flow rate. Hereby, the particles in the bed can be forced to shift around to obtain a more suitable packing geometry and remove the need to unpack the bed. In this case the process is returned to step S12, testing, after the conditioning to see if the bed properties have been improved.

S17: Based on the test results a new filling height is calculated, i.e. if the test showed that the media bed was not packed well enough the slurry volume or the slurry concentration filled into the column can be modified in order to achieve an improved packed bed. A further possibility to change packing conditions in order to improve the packed bed properties would be to change the adapter speed during packing. Possibly a new automatic measure of the slurry concentration can also be performed in order to calculate a new filling height. Thereafter the procedure is repeated from step S7 (filling slurry into the column).

Hereby the control unit 15 comprises according to the invention software such that the start and stop of these steps (some of them optionally) can be controlled automatically without any manual interactions. An operator preferably provides input data to the control unit 15 or chooses data from a pre-programmed list before the packing process is started. Said data can be information regarding the actual packing to be performed such as for example media type, target bed height, column diameter, test conditions (type of test, sample, solvent, sample volume, test speed), packing factor and for example flow and pressure controlled by the process system. Hereby the whole packing process including testing, unpacking and re-packing can be fully automated.

The control unit 15 can also comprise software for guiding the user through the packing procedure. It can comprise a graphical user interface in which the user can follow the packing procedure and possibly also interrupt the procedure and control one or more parts of the process manually.

In one embodiment of the invention safety features such as means for monitoring for example over-pressurizing of the column or over-compressing of the medium can be included to ensure safe and fail proof operation. These monitoring means could be for example pressure gauges in liquid connection with the inside of the column, flow meters to control flow, air sensors to reduce the risk of applying air into the column, but also means to detect the amount of force that is applied onto the bed.

Although, the invention has been illustrated by examples of embodiments in which the column is cylindrical and has a constant diameter, which enables a linear correlation between cylinder volume and bed height, it is also conceivable to adapt the present invention for application to other column shapes in which the correlation is non-linear. It could be for example radial columns or other shapes.

Even though the present invention has been described above in terms of specific embodiments, many modification and variations of this invention can be made as will be obvious to those skilled in the art, without departing from its spirit and scope as set forth in the following claims.

What is claimed is:

1. A method for automatically without any required manual interaction packing a media bed in a column (3) from a slurry being a dispersion of said media particles and a liquid, said method comprising the steps a)-f) which all are performed automatically:
   a) filling the column (3) with a certain volume of slurry;
   b) packing a media bed from the slurry to a predefined target bed height or a predefined target bed compression;
   c) testing the separation efficiency of the packed bed;
   d) automatically unpacking the bed if test results not are acceptable or alternatively flow conditioning the packed bed if test results not are acceptable and return to c);
   e) calculating new volume of slurry to be filled into the column based on the test results; and
   f) repeat from a).

2. The method of claim 1, further comprising the step of automatically priming and/or sanitizing the column before filling the column with slurry.

3. The method of claim 1, further comprising the step of automatically calculating the volume of slurry to be filled into the column given data entered by the user and/or data measured inline.

4. The method of claim 1, further comprising the step of automatically rinsing the hoses after filling the column with slurry and before packing is started.

5. The method of claim 1, wherein the testing can be a pulse test, a transitional test, a pressure/flow test, a stability test and/or a void measurement.

6. The method of claim 1, further comprising the step of automatic sanitization of the packed column and/or providing the packed column in a storage solution if test results in step d) are acceptable.

* * * * *